(12) United States Patent
Fisher

(10) Patent No.: US 6,916,051 B2
(45) Date of Patent: Jul. 12, 2005

(54) COUPLER FOR A FLEXIBLE TUBE

(75) Inventor: Mark Fisher, Sellersville, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 10/767,896

(22) Filed: Jan. 28, 2004

(65) Prior Publication Data

US 2004/0183305 A1 Sep. 23, 2004

Related U.S. Application Data

(60) Provisional application No. 60/447,115, filed on Feb. 13, 2003.

(51) Int. Cl.[7] .............................................. F16L 17/00
(52) U.S. Cl. ...................... 285/373; 285/371; 285/921
(58) Field of Search ........................... 285/371, 15, 82, 285/53, 148.17, 294.1, 294.4, 369, 373, 419, 921, 124.1; 604/905, 533

(56) References Cited

U.S. PATENT DOCUMENTS

| | | | |
|---|---|---|---|
| 4,340,052 A | | 7/1982 | Dennehey et al. |
| 4,405,312 A | * | 9/1983 | Gross et al. ................. 604/533 |
| 4,432,759 A | * | 2/1984 | Gross et al. ................. 285/419 |
| 4,895,570 A | | 1/1990 | Larkin |
| 5,059,170 A | | 10/1991 | Cameron |
| 5,171,216 A | | 12/1992 | Dasse et al. |
| 5,431,641 A | | 7/1995 | Grözinger et al. |
| 5,443,096 A | * | 8/1995 | King ........................... 285/373 |
| 5,531,695 A | | 7/1996 | Swisher |
| 6,267,754 B1 | | 7/2001 | Peters |

* cited by examiner

*Primary Examiner*—Aaron Dunwoody
(74) *Attorney, Agent, or Firm*—Joseph E. Maenner; Monte & McGraw, P.C.

(57) ABSTRACT

A coupler for a flexible tube is disclosed. The coupler includes a first channeled member having a generally semicircular cross-section and a first longitudinal axis extending therethrough and a second channeled member having a generally semicircular cross-section and a second longitudinal axis extending therethrough. The first longitudinal axis is generally parallel to the second longitudinal axis. A hinge connects a first length of the first channeled member to a first length of the second channeled member. A lateral axis generally bifurcates the first length of the first channeled member and the first length of the second channeled member. A plurality of barbs are disposed in each of the first and second channeled members, wherein each barb extends generally toward an intersection of the longitudinal axis of its respective channeled member and the lateral axis. A lock secures a second length of the first channeled member to a second length of the second channeled member.

13 Claims, 9 Drawing Sheets

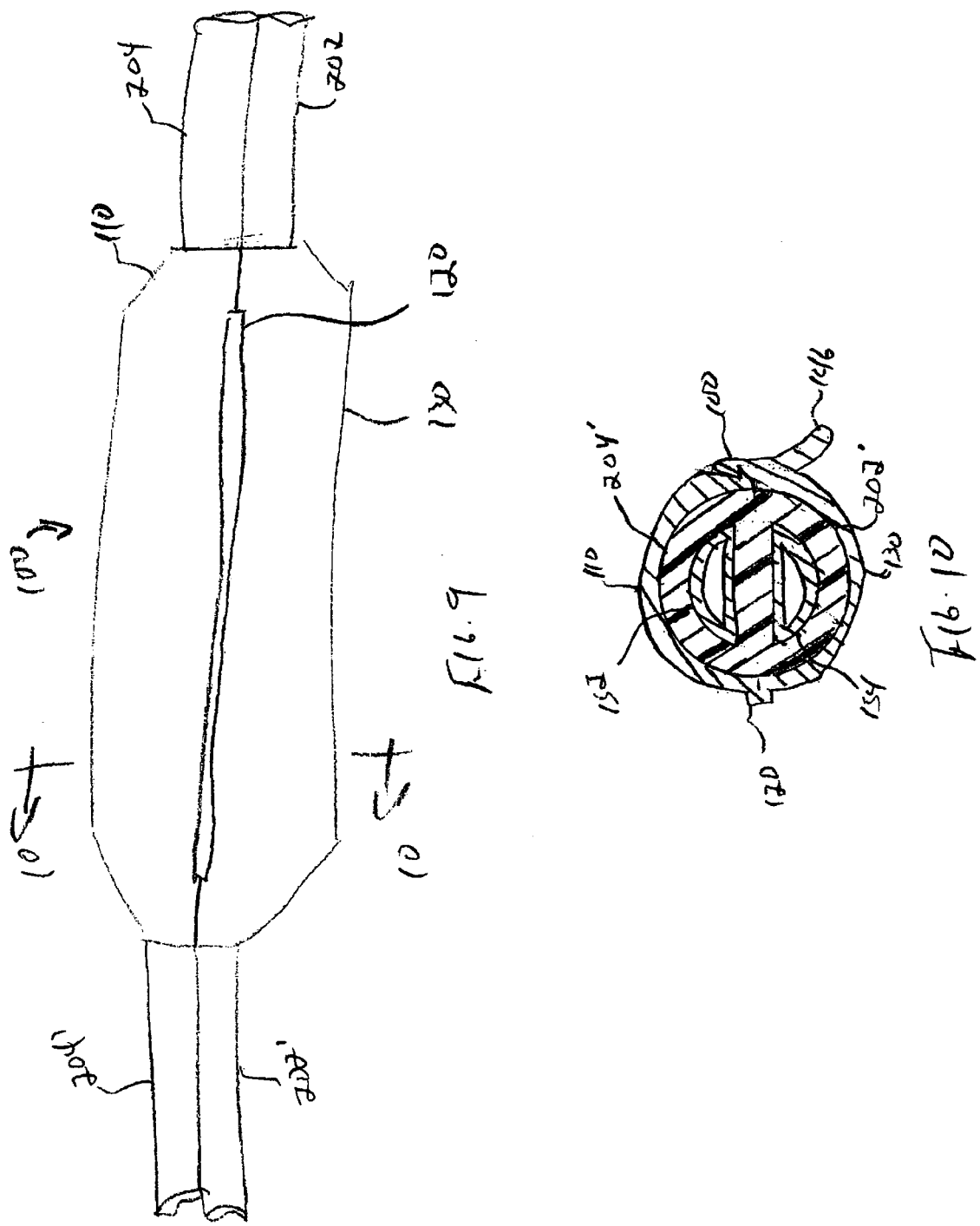

COUPLER FOR A FLEXIBLE TUBE

CROSS REFERENCE TO RELATED APPLICATION

The present application claims priority from U.S. Provisional Patent Application Ser. No. 60/447,115, filed Feb. 13, 2003.

FIELD OF THE INVENTION

The present invention relates to a coupler that is used to repair a flexible conduit, such as a catheter.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical multiple lumen catheter is a dual lumen catheter in which one lumen introduces fluid and the other lumen removes fluid. An example of such a multiple lumen catheter assembly is the SPLIT-CATH® catheter. Catheterization may also be performed by using separate, single lumen catheters inserted through two different incisions into an area to be catheterized. An example of such a catheter assembly is a TESIO® catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the end portion of the guide wire that has been inserted into the vessel within the vessel and the opposing end of the guide wire projecting beyond the surface of the skin of the patient. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator and sheath device is passed over the guide wire to enlarge the hole. The dilator and the guide wire are then removed from the sheath, leaving only the sheath. The catheter is then inserted through the sheath and into the vessel. The sheath is then removed from around the catheter by tearing the sheath as the sheath is being removed from the patient.

For chronic catheterization, in which the catheter is intended to remain inside the patient for extended period of time, such as for weeks or even months, it is typically desired to subcutaneously tunnel the catheter into a patient using various tunneling techniques. The catheter is typically tunneled into the patient prior to inserting the catheter into the patient's vein. The subcutaneous tunnel provides a stable anchor to prevent the proximal end of the catheter from moving and possibly becoming dislodged, which could result in patient injury or death. An anchoring cuff typically circumscribes a portion of the catheter assembly that is located within the tunnel, allowing skin tissue to grow in and around the cuff, further stabilizing the catheter.

Catheter assemblies typically include a hub that connects a proximal end of each catheter lumen with a distal end of an extension tube. Occasionally, a blood clot may form in a catheter lumen at a junction between the catheter lumen and the hub, cutting off blood flow through the catheter lumen. Such an occasion typically necessitates removal of the entire catheter assembly from the patient, including insertion of a new catheter assembly in place of the failed catheter assembly. Part of this removal includes separating the skin from the cuff in the subcutaneous tunnel, and pulling the catheter assembly through the tunnel, as well as removing the catheter lumens from the patient's blood vessel. The removal of the failed catheter assembly and the insertion of the new catheter assembly causes additional trauma to the patient, which is not desired.

It would be beneficial to be able to repair a clogged catheter lumen without having to remove the entire catheter assembly from the patient and inserting a new catheter assembly.

BRIEF SUMMARY OF THE INVENTION

Briefly, the present invention provides a coupler for a flexible tube. The coupler includes a first channeled member having a generally semicircular cross-section and a first longitudinal axis extending therethrough and a second channeled member having a generally semicircular cross-section and a second longitudinal axis extending therethrough. The first longitudinal axis is generally parallel to the second longitudinal axis. A hinge connects a first length of the first channeled member to a first length of the second channeled member. A lateral axis generally bifurcates the first length of the first channeled member and the first length of the second channeled member. A plurality of barbs are disposed in each of the first and second channeled members, wherein each barb extends generally toward an intersection of the longitudinal axis of its respective channeled member and the lateral axis. A locking means secures a second length of the first channeled member and a second length of the second channeled member.

Further, the present invention provides a coupler assembly for a flexible conduit. The coupler assembly comprises an exterior coupler adapted to fit over an exterior of a flexible conduit. The exterior coupler comprises a first member having a first longitudinal axis extending therethrough and a generally semicircular first channel extending along the first longitudinal axis and a second member having a second longitudinal axis extending therethrough and a generally semicircular second channel extending along the second longitudinal axis. The first longitudinal axis is generally parallel to the second longitudinal axis. A hinge connects a first length of the first member to a first length of the second member. A lateral axis generally bifurcates the first length of the first member and the first length of the second member. A plurality of barbs are disposed in each of the first and second channels. Each barb extends generally toward an intersection of the longitudinal axis of its respective channeled member and the lateral axis. Locking means are adapted to retain both the first and second members over the exterior of the flexible conduit. A support member is adapted to be inserted into an interior of the flexible conduit, generally within the exterior coupler.

Additionally, the present invention provides a method of repairing a leak in a flexible conduit. The method comprises severing the flexible conduit proximate to the leak, forming a first conduit portion and a second conduit portion; inserting a first end of an internal support into the first conduit portion; inserting a second end of the internal support into the second conduit portion; disposing a conduit clamp over the first conduit portion, the second conduit portion, and the internal support, wherein the conduit clamp comprises a first clamp portion; a second clamp portion; a hinge flexibly connecting the first clamp portion to the second clamp portion; and means for locking the first clamp portion to the second clamp portion, distal from the hinge; and engaging the means for locking the first clamp portion to the second clamp portion.

BRIEF DESCRIPTION OF THE DRAWINGS

The accompanying drawings, which are incorporated herein and constitute part of this specification, illustrate a presently preferred embodiment of the invention, and, together with the general description given above and the detailed description given below, serve to explain the features of the invention. In the drawings:

FIG. 9 is a side view, in elevation, of the coupler of FIG. 8 in a closed position.

FIG. 10 is a sectional view of the coupler taken along line 10—10 of FIG. 9.

DETAILED DESCRIPTION OF THE PRESENT INVENTION

Figure 1:
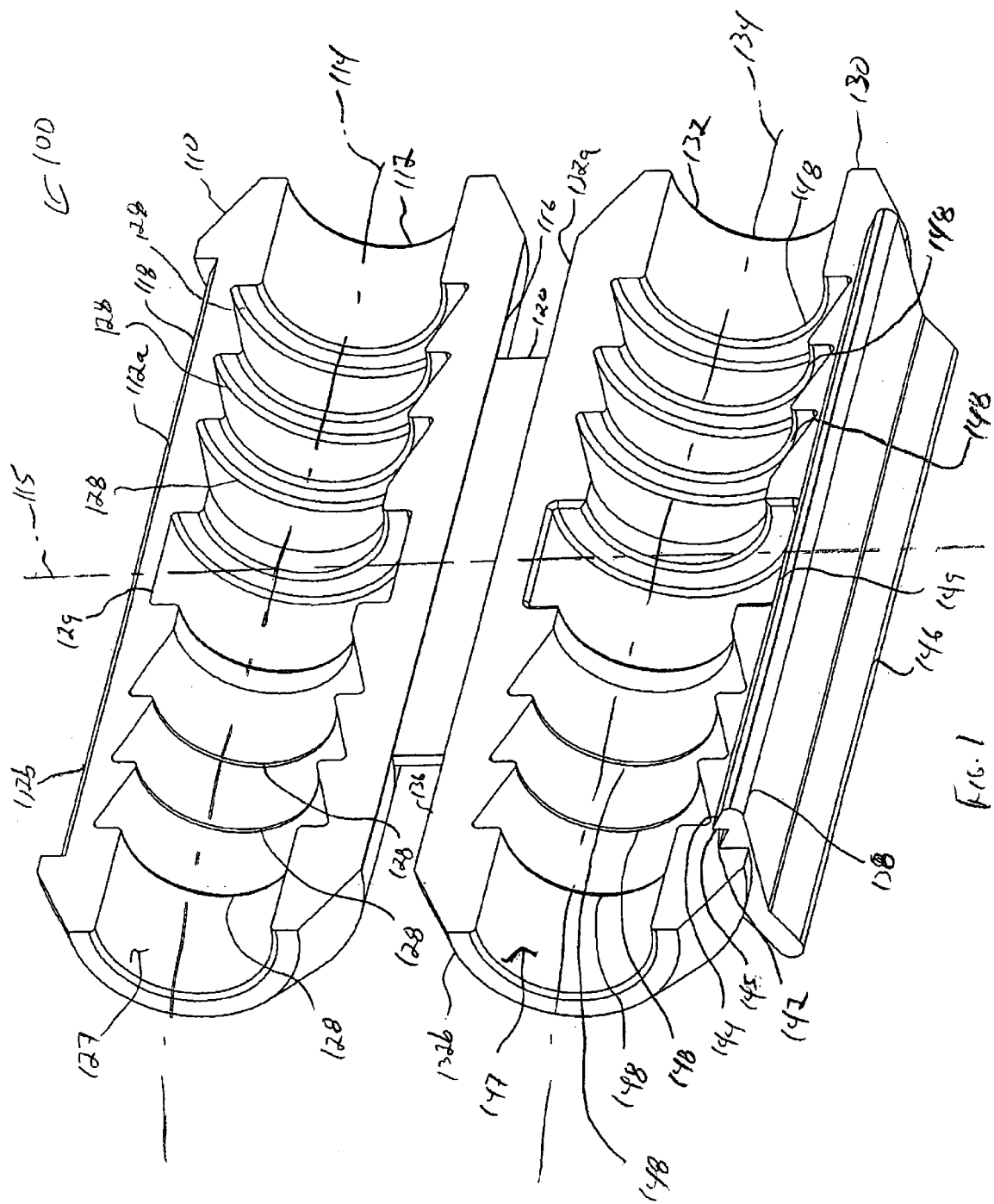
FIG. 1 is a front perspective view of a catheter coupler according to a preferred embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of a catheter that utilizes the coupler according to the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

Figure 2:
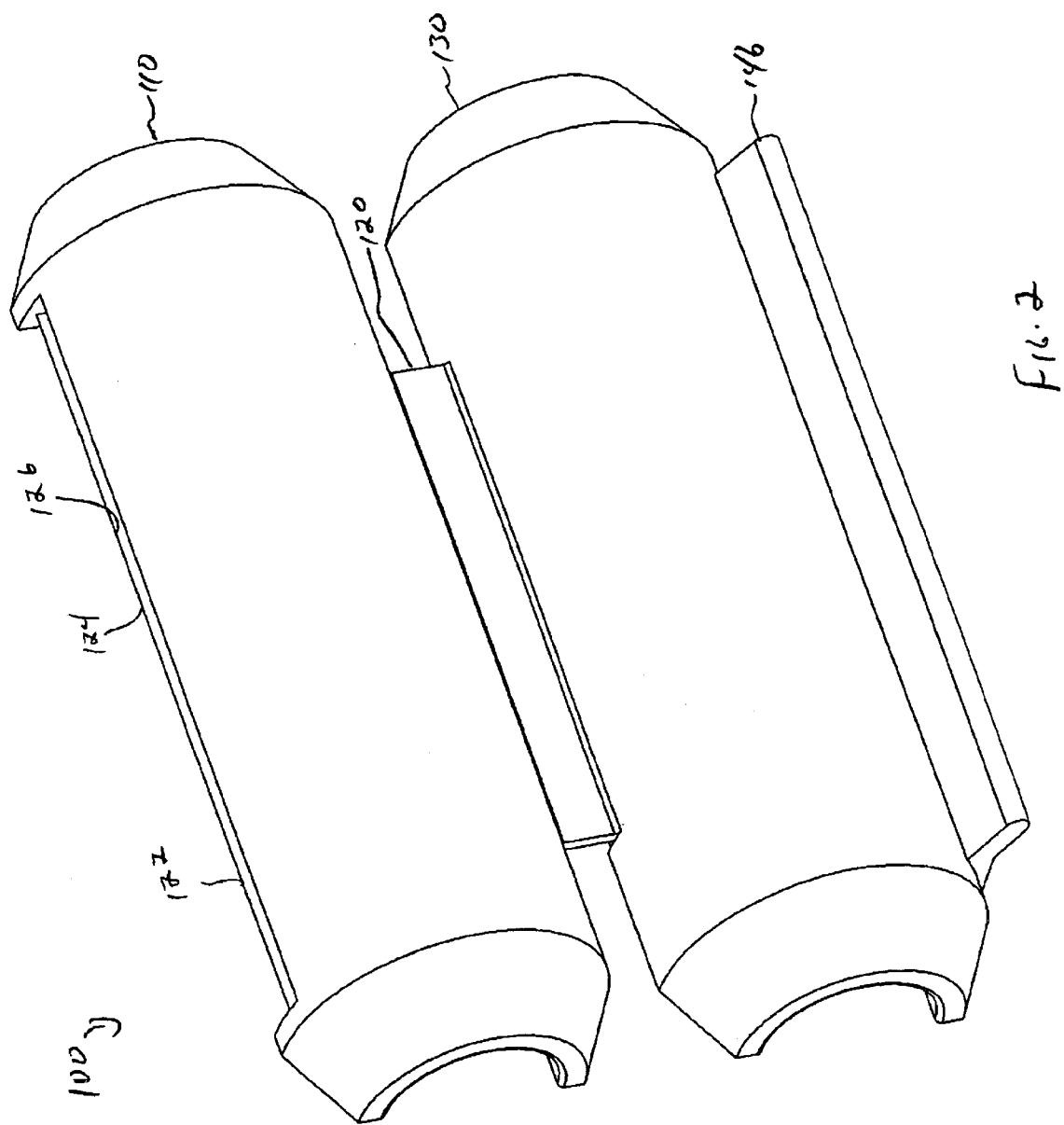
FIG. 2 is a rear perspective view of the catheter coupler shown in FIG. 1.
Figure 3:
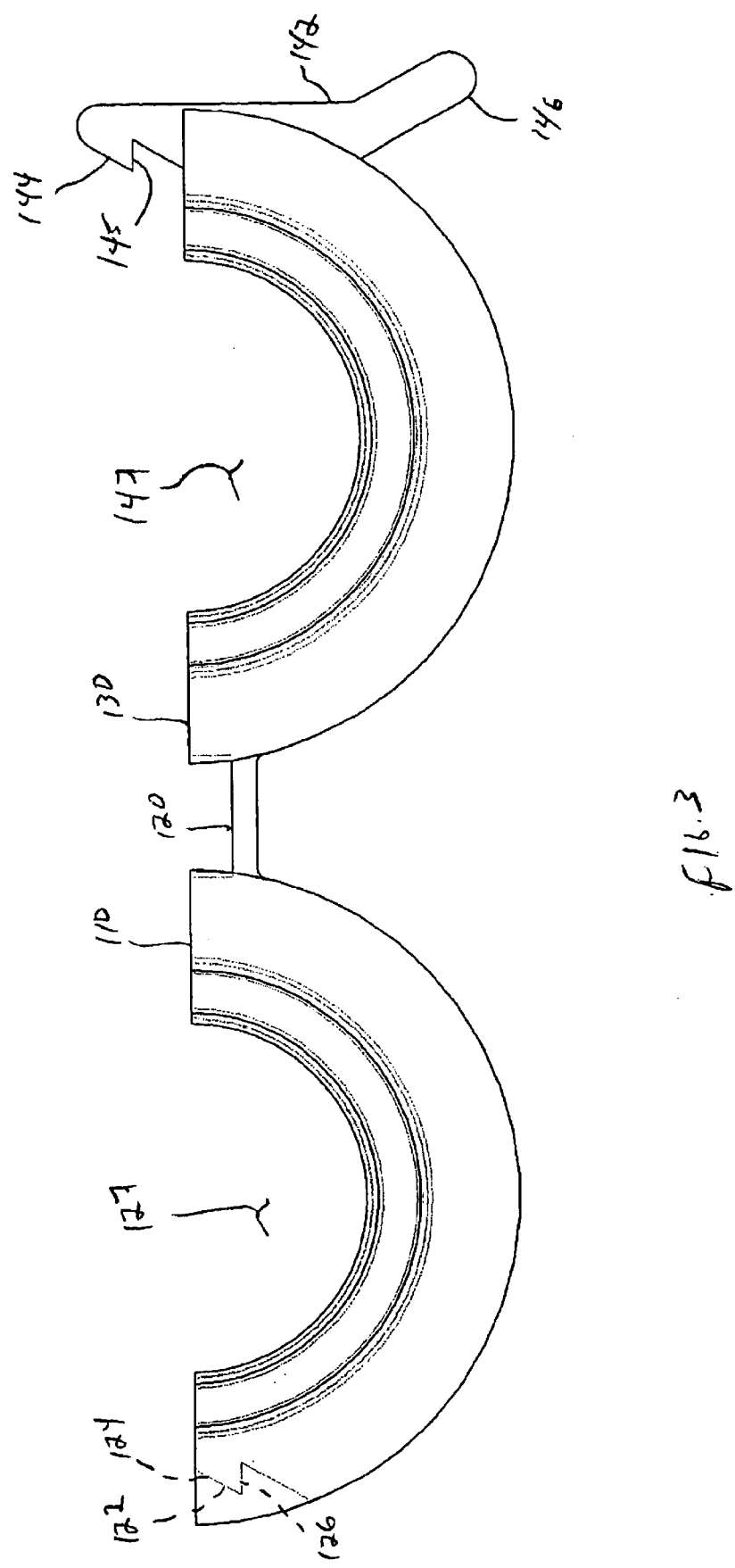
FIG. 3 is an end view of the catheter coupler shown in FIG. 1.

Referring now to FIGS. 1–3, a catheter repair coupler 100 according to the present invention is shown. The coupler 100 includes a first portion 110 and a second portion 130. The first portion 10 includes a generally elongated semi-tubular first body 112 having a longitudinal axis 114 extending therethrough. A lateral axis 115 extends generally perpendicular to the longitudinal axis 114. Preferably, the lateral axis 115 generally bifurcates the first body 112 into a first lateral portion 112a and a second lateral portion 112b, such that the first and second lateral portions 112a, 112b are generally mirror images of each other.

The first body 112 includes a first connected length 116 and a first locking length 118. The first connected length 116 and the first locking length 118 are both generally parallel to the longitudinal axis 114. At least a portion of the first connected length 116 is connected to a hinge 120 that connects the first portion 110 and the second portion 130.

Referring now to FIG. 2, the first locking length 118 includes a lip 122 that extends along at least a portion, and preferably, a major portion, of the first locking length 118. The lip 122 includes a beveled face 124 and an adjoining cantilevered face 126.

Referring back to FIG. 1, a first channel 127 extends along the longitudinal axis 114 so that a cross-section or an end view of the body 112, as seen in FIG. 3, is generally semi-circular in shape. A plurality of generally semi-circular barbs 128 extend along the first channel 127, generally toward an intersection of the longitudinal axis 114 and the lateral axis 115. As shown in FIG. 1, preferably three barbs 128 are disposed on either side of the lateral axis 115, although those skilled in the art will recognize that more or less than three barbs 128 may be used. A generally semi-circular first recess 129 extends generally along the lateral axis 115, with preferably three barbs 128 on either side of the first recess 129.

The second portion 130 is similar to the first portion 110, with a generally elongated semi-tubular second body 132 and a longitudinal axis 134 extending therethrough. The lateral axis 115 extends generally perpendicular to the longitudinal axis 134. Preferably, the lateral axis 115 generally bifurcates the second body 132 into a first lateral portion 132a and a second lateral portion 132b, such that the first and second lateral portions 132a, 132b are generally mirror images of each other.

The second body 132 includes a second connected length 136 and a second locking length 138. The second connected length 136 and the second locking length 138 are both generally parallel to the longitudinal axis 134. At least a portion of the second connected length 136 is connected to the hinge 120 that connects the first portion 110 to the second portion 130.

Referring now to FIGS. 1 and 3, the second locking length 138 includes a tab 142 that extends along at least a portion, and preferably, a major portion, of the second locking length 138. The tab 142 includes a beveled face 144 and an adjoining cantilevered face 145. The tab 142 complements the lip 122 so that the tab 142 engages the lip 122 in locking engagement, as is described in more detail later herein. A lever 146 extends generally obliquely away from and is preferably generally the same length as the tab 142. The lever 146 is disposed to bias the tab 142 away from the lip 122 to unlock the first locking length 118 from the second locking length 138.

A second channel 147 extends along the longitudinal axis 134 so that a cross-section of the body 132, as seen in FIG. 3, is generally semi-circular in shape. Referring back to FIG. 1, a plurality of generally semi-circular barbs 148 extend along the second channel 147, generally toward an intersection of the longitudinal axis 134 and the lateral axis 115. As shown in FIG. 1, preferably three barbs 148 are disposed on either side of the lateral axis 115, although those skilled in the art will recognize that more or less than three barbs 148 may be used. A generally semi-circular second recess 149 extends generally along the lateral axis 115, with preferably three barbs 148 on either side of the second recess 149.

The hinge 120 is preferably a living hinge that flexibly connects the first portion 110 to the second portion 130. Preferably, the hinge 120 extends generally along a major length of each of the first connected length 116 of the first portion 110 and the second connected length 136 of the second portion 130. Preferably, the coupler 100 is of unitary construction and is manufactured from a polymer, or some other suitable material. More preferably, the coupler 100 is constructed from polypropylene.

Figure 4:
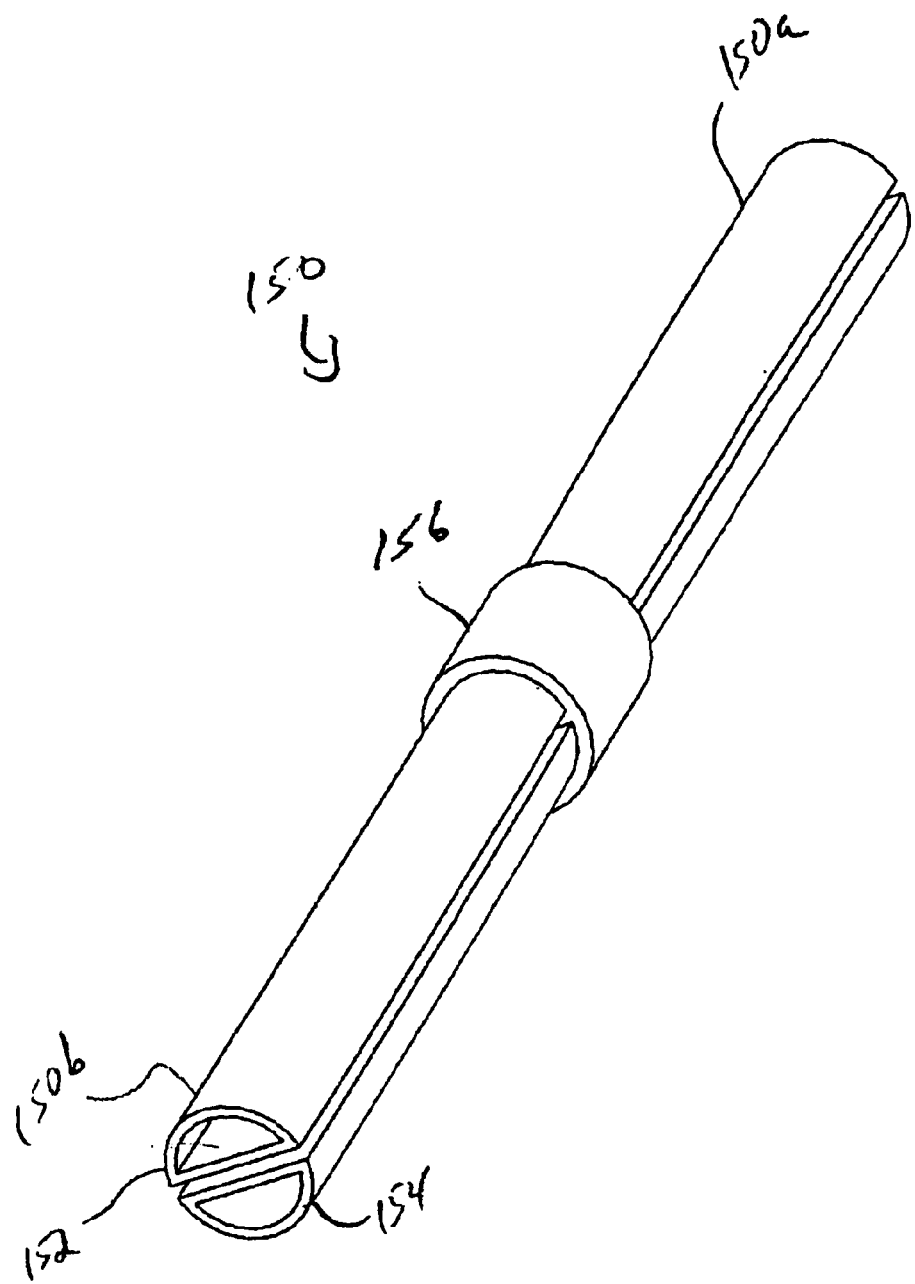
FIG. 4 is a perspective view of a first preferred embodiment of a coupler insert for use with the catheter coupler of FIG. 1.
Figure 5:
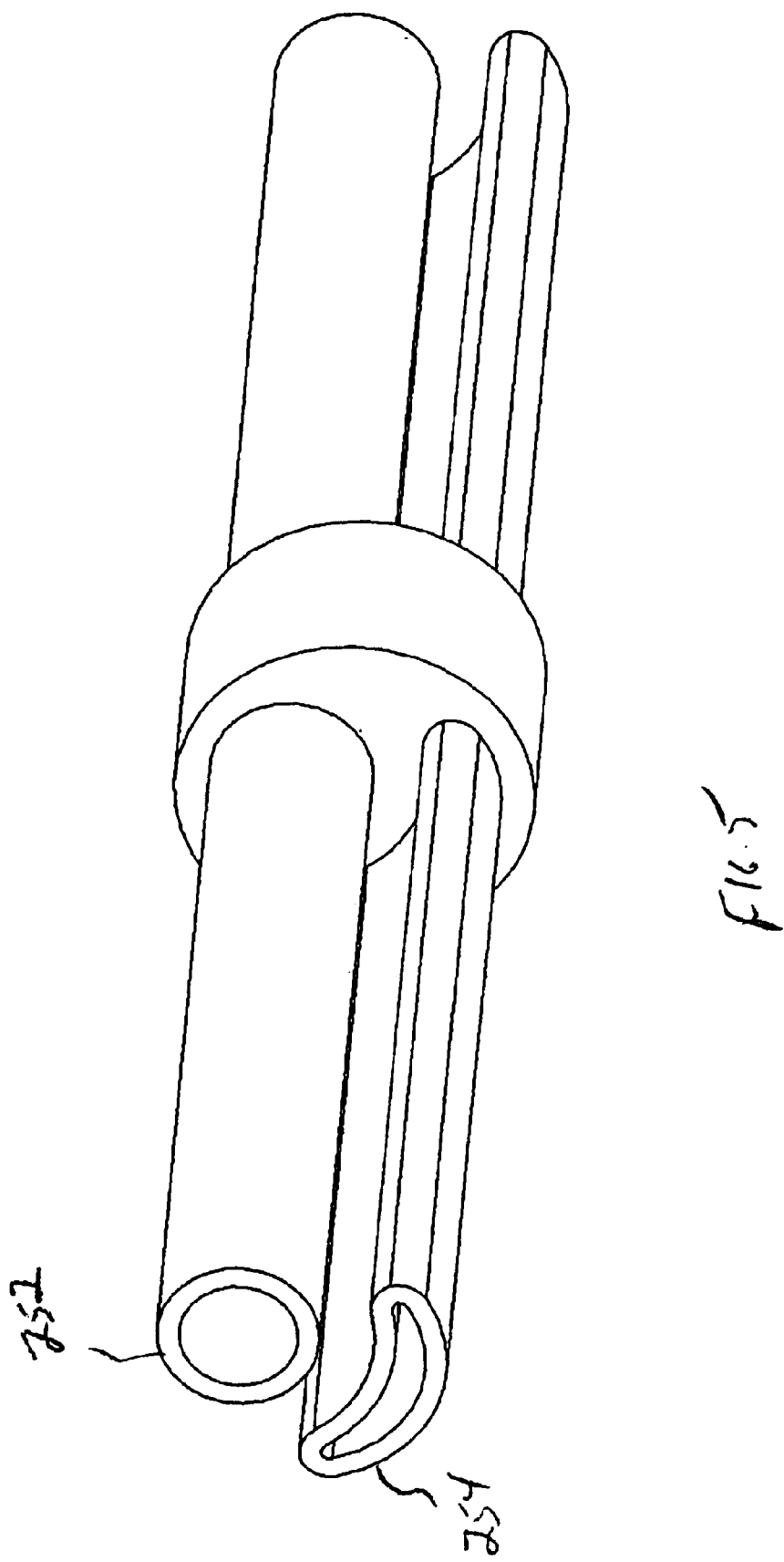
FIG. 5 is a perspective view of a second preferred embodiment of a coupler insert for use with the catheter coupler of FIG. 1.

A coupler insert 150, shown in FIG. 4, is used with the coupler 100 to provide additional strength to the coupler 100. Preferably, the coupler insert 150 is generally tubular in shape and has a distal insert end 150a and a proximal insert end 150b. The coupler insert 150 includes a coupler insert lumen 152, 154 sized and shaped for insertion into each catheter lumen. As seen in FIG. 4, the coupler insert 150 includes two insert lumens 152, 154, with juxtaposed D-shaped lumens to fit into catheter lumens of an SPLIT-CATH® catheter. However, those skilled in the art will recognize that the insert lumens 152, 154 may be other shapes to fit into lumens of other catheters, and that more or less than two insert lumens 152, 154 may be used, depending on the number of catheter lumens in the catheter assembly being repaired. For example, an alternative embodiment of the insert is shown in FIG. 5 as insert 250. The insert 250 includes a circular lumen 252 and a crescent-shaped lumen 254 to conform to lumens in a catheter such as the HEMO-FLOW™ catheter (not shown). Referring back to FIG. 4, the insert lumens 152, 154 are open, allowing for fluid communication between the distal insert end 150a and the proximal insert end 150b.

Referring still to FIG. 4, the coupler insert 150 includes a collar 156 that circumferentially extends around a portion of the coupler inset 150, and that is located preferably generally approximately half way between the distal insert end 150a and the proximal insert end 150b. Also preferably, the coupler insert 150 is approximately the same length as the coupler 100. Preferably, the coupler insert 150 is constructed from stainless steel or some other suitable, biocompatible material.

Figure 6:
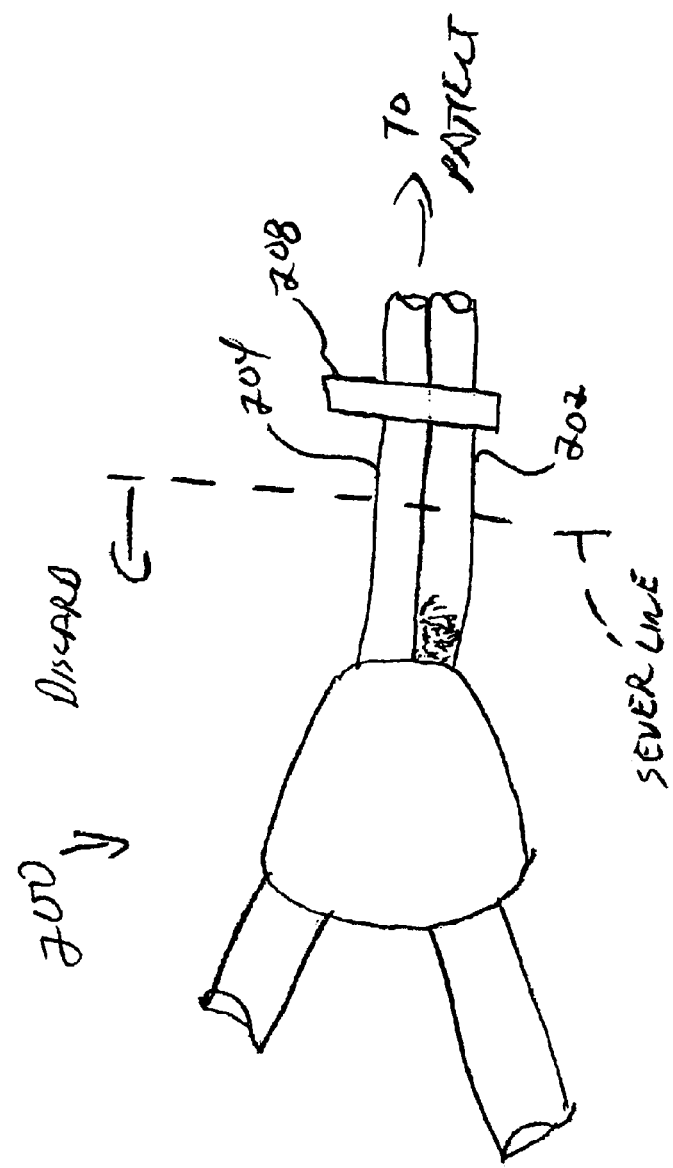
FIG. 6 is a front view, in elevation, of a clogged catheter being severed to allow the coupler and coupler insert of FIGS. 1 and 4, respectively, to repair the catheter.

Operation of the coupler 100 is now described. In the event of a failure of a catheter assembly 200 having two catheter lumens 202, 204, along one of the catheter lumens 202, 204, such as a failure caused by a leak in one of the catheter lumens 202, 204 or a blood clot clogging the catheter lumen 202, as shown in FIG. 6, the catheter assembly 200 is clamped off with a clamp 208 distal to the failure. The catheter lumens 202, 204 are severed between the failure and the clamp 208, and the failed portion is discarded.

Figure 7:
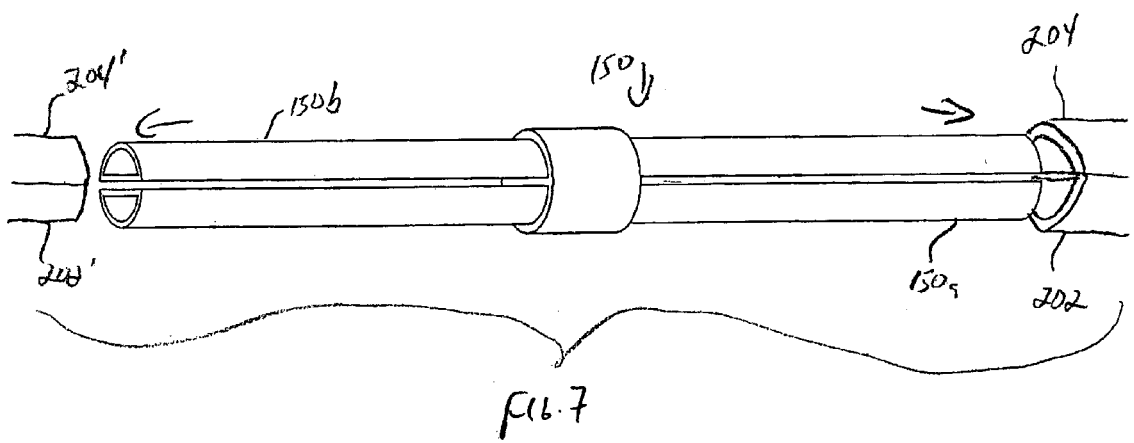
FIG. 7 is a perspective view of the coupler insert of FIG. 4 being used to couple proximal and distal ends of a catheter assembly.

Referring to FIG. 7, coupler inserts 150 are connected to the proximal ends of the catheter lumens 202, 204 by inserting the distal insert end 150a of each coupler insert 150 into the proximal end of a catheter lumen 202, 204. The proximal insert end 150b of the coupler insert 150 is inserted into the distal end of a new proximal portion of catheter lumens 202', 204'. The distal and proximal insert ends 150a, 150b are sized to provide an interference fit with the insides of the catheter lumens 202, 204, 202', 204' to help seal the catheter lumens 202, 204, 202', 204' against leakage.

Figure 8:
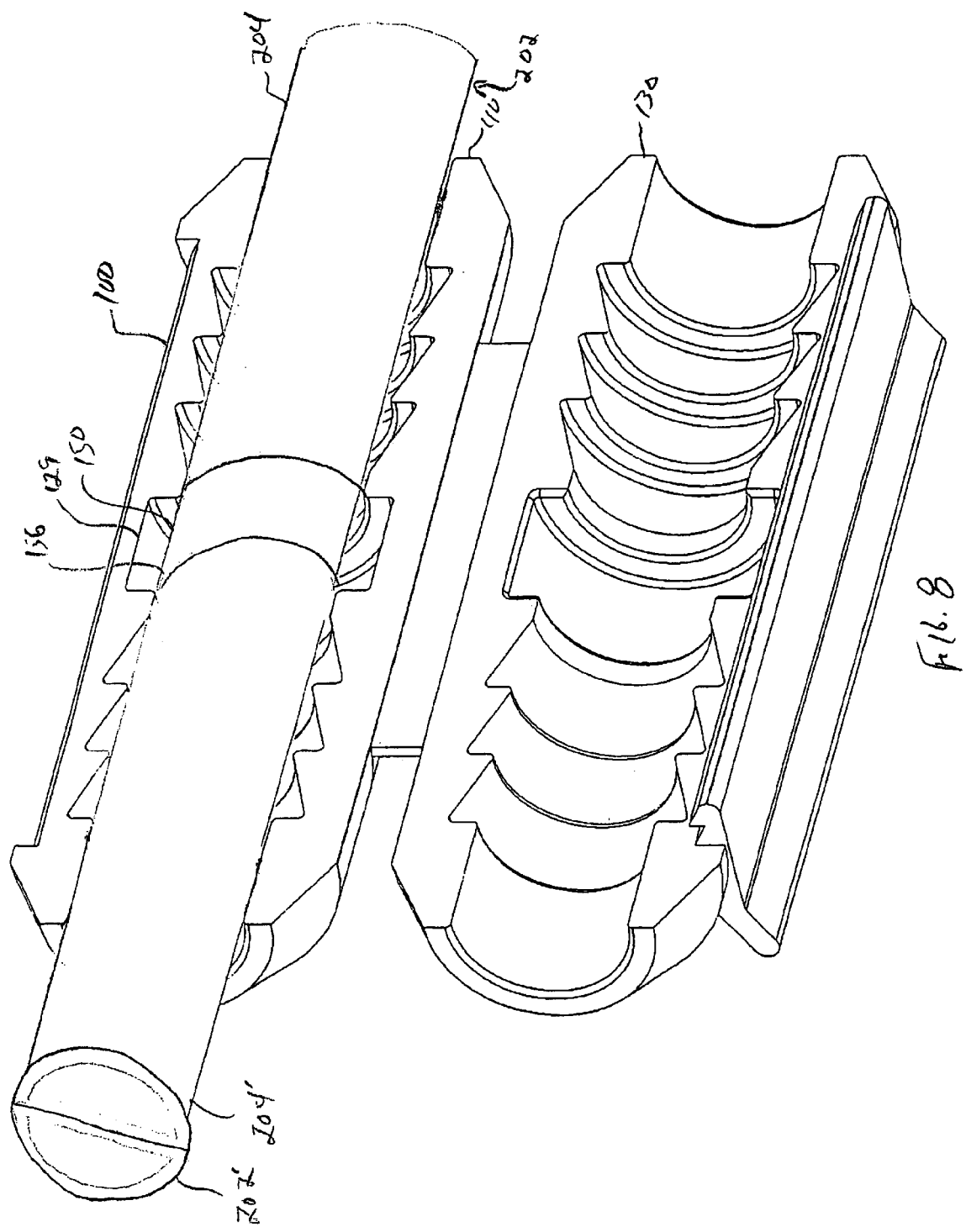
FIG. 8 is a perspective view of the proximal and distal ends of the catheter assembly of FIG. 7 being inserted into the coupler of FIG. 1.

Referring now to FIG. 8, the coupler 100 is next disposed over the coupler insert 150 and the catheter lumens 202, 204, 202', 204' inside of which the coupler insert 150 has been inserted. The catheter lumens 202, 204, 202', 204' are disposed within the first channel 127, with the collar 156 being inserted into the first recess 129. The second portion 130 is pivoted about the hinge 120 such that the catheter lumens 202, 204, 202', 204' are disposed within the second channel 147 and the second recess 149 envelopes a portion of the collar 156.

The beveled face 144 of the tab 142 engages the beveled face 124 of the lip 122, biasing the tab 142 away from the longitudinal axis 134 of the second portion 130. As the second portion 130 is further pivoted about the hinge 120, the beveled face 144 of the tab clears the beveled face 124 of the lip 122, and the beveled face 144 of the tab 142 snaps back toward its unbiased position. The cantilevered face 145 of the tab 142 engages the cantilevered face 126 of the lip 122, locking the tab 142 to the lip 122, and connecting the first locking length 118 of the first portion 110 and the second locking length 138 of the second portion 130 together.

As the second portion 130 is being pivoted about the hinge 120, the barbs 128, 148 in each of the first and second channels 127, 147 engage the exterior of the catheter lumens 202, 204, 202', 204' and compress the catheter lumens 202, 204, 202', 204' toward the connector insert 150. The barbs 128, 148 dig in to the catheter lumens 202, 204, 202', 204' to prevent the catheter lumens 202, 204, 202', 204' from being pulled out of the coupler 100 along either the first or second longitudinal axes 114, 134. FIGS. 9 and 10 show the coupler 100 in a closed position, coupling the lumens 202, 204 and the lumens 202', 204'.

In the event that it is desired to open the coupler 100 after the coupler 100 is locked, the lever 146 may be pushed in the direction of the arrow shown in FIG. 10 to release the tab 142 away from the lip 122. When the tab 142 is moved away from the lip 122 sufficiently so that the cantilevered face 145 of the tab 142 clears the cantilevered face 126 of the lip 122, releasing the tab 142 from the lip 122, the second portion 130 may be rotated about the hinge 130, opening the coupler 100 and allowing the catheter lumens 202, 204, 202', 204' to be removed from the coupler 100.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A coupler for first and second lengths of flexible tube, comprising:
   a first and second lengths of flexible tube;
   a first channeled member having a first lateral portion, a second lateral portion, a generally semicircular cross-section and a first longitudinal axis extending therethrough;
   a second channeled member having a generally semicircular cross-section and a second longitudinal axis extending therethrough, wherein the first longitudinal axis is generally parallel to the second longitudinal axis;
   a hinge connecting a first length of the first channeled member and a first length of the second channeled member;
   a lateral axis generally bifurcating the first length of the first channeled member and the first length of the second channeled member;

a plurality of barbs disposed in each of the first and second lateral portions, wherein each barb extends generally toward an intersection of the first longitudinal axis and the lateral axis; and a locking member securing a second length of the first channeled member to a second length of the second channeled member to enable the first and second lengths of flexible tube to be retained within a chamber formed when the second length of the first channeled member is secured to the second length of the second channeled member such that the barbs in the first lateral portion engage the first length of flexible tube and the barbs in the second lateral portion engage the second length of flexible tube.

2. The coupler according to claim 1, wherein the locking member comprises a first tab that extends along at least a portion of the second length of the first channeled member and a complementary up that extends along at least a portion of the second length of the second channeled member, wherein the tab is engageable with the lip.

3. The coupler according to claim 2, wherein the tab further comprises a lever disposed along at least a portion of the tab, wherein displacement of the tab in a first direction releases the tab from the lip.

4. The coupler according to claim 1, wherein the first and second lateral portions are generally mirror images of each other.

5. The coupler according to claim 1, wherein the coupler is of unitary construction.

6. The coupler according to claim 1, wherein the coupler is constructed from a polymer.

7. The coupler according to claim 1, further comprising a generally tubular channel in each of the first and second channeled members proximate to the lateral axis.

8. The coupler according to claim 1, wherein the hinge is a living hinge.

9. A coupler assembly for first and second lengths of a flexible conduit, comprising:

a first and second lengths of flexible tube;

an exterior coupler adapted to fit over an exterior of a said first and second lengths of flexible conduit, wherein the exterior coupler comprises:

a first member having a first longitudinal axis extending therethrough, a first lateral portion, a second lateral portion, and a generally semicircular first channel extending along the first longitudinal axis;

a second member having a second longitudinal axis extending therethrough and a generally semicircular second channel extending along the second longitudinal axis, wherein the first longitudinal axis is generally parallel to the second longitudinal axis;

a hinge connecting a first length of the first member and a first length of the second member;

a lateral axis generally bifurcating the first length of the first member and the first length of the second member;

a plurality of barbs disposed in each of the first and second lateral portions, wherein each barb extends generally toward an intersection of the first longitudinal axis and the lateral axis; and a locking member adapted to retain both the first and second members over the exterior of the first and second lengths of the flexible conduit; and a support member adapted to be inserted into an interior each of the first and second lengths of the flexible conduit, generally within the exterior coupler.

10. The coupler assembly according to claim 9, wherein the flexible conduit is a catheter lumen.

11. The coupler assembly according to claim 9, wherein the exterior coupler is of unitary construction.

12. The coupler assembly according to claim 9, wherein the coupler is constructed from a polymer.

13. The coupler assembly according to claim 9, wherein the hinge is a living hinge.

* * * * *